US012806398B2

(12) United States Patent
Nandakumar et al.

(10) Patent No.: US 12,806,398 B2
(45) Date of Patent: Nov. 24, 2026

(54) NON-DISCONNECTING ROTATABLE CONNECTOR ASSEMBLY

(71) Applicant: CareFusion 303, Inc., San Diego, CA (US)

(72) Inventors: Sridhaar Nandakumar, Chennai (IN); Rahul Rajan Puthukkad, Bengaluru (IN); Arjun Murali, Bangalore (IN); Suhas Hanumantharao, Bengaluru (IN); Arun Karthik Senthil Murugan, Bangalore (IN)

(73) Assignee: CAREFUSION 303, INC., San Diego, CA (US)

( * ) Notice: Subject to any disclaimer, the term of this patent is extended or adjusted under 35 U.S.C. 154(b) by 413 days.

(21) Appl. No.: 18/525,173

(22) Filed: Nov. 30, 2023

(65) Prior Publication Data

US 2025/0180147 A1 Jun. 5, 2025

(51) Int. Cl.

*A61M 39/10* (2006.01)
*F16L 37/098* (2006.01)
*F16L 37/53* (2006.01)

(52) U.S. Cl.

CPC .... *A61M 39/1011* (2013.01); *A61M 39/1055* (2013.01); *F16L 37/0982* (2013.01);
(Continued)

(58) Field of Classification Search

CPC ...... A61M 39/1011; A61M 2039/1033; A61M 2039/1066; A61M 2039/1027;
(Continued)

(56) References Cited

U.S. PATENT DOCUMENTS 7,857,805 B2 12/2010 Raines
9,933,094 B2 4/2018 Fangrow
(Continued)

FOREIGN PATENT DOCUMENTS

CA 2606834 A1 * 4/2008 ........ A61M 39/1011
EP 3004711 B1 7/2018
(Continued)

OTHER PUBLICATIONS

International Search Report and Written Opinion for Application No. PCT/US2024/050589, dated Jan. 20, 2025, 11 pages.

*Primary Examiner* — Wesley G Harris
(74) *Attorney, Agent, or Firm* — MASCHOFF BRENNAN

(57) ABSTRACT

A connector including a housing having a first end and second end opposite the first end, the housing having an interior space, a luer assembly disposed within the interior space of the housing, the luer assembly having a locking ring and the luer assembly configured to couple to a coupling device to secure the coupling device to the connector, and a sleeve at least partially disposed around the luer assembly and disposed within the interior space, the sleeve configured to couple to the locking ring to prevent axial movement of the sleeve relative to the luer assembly and the housing. The housing being rotatable to the luer assembly and the sleeve when the sleeve is coupled to the locking ring to prevent decoupling of the luer assembly from the coupling device when the luer assembly is coupled to the coupling device.

19 Claims, 16 Drawing Sheets

(52) U.S. Cl.
CPC .............. *F16L 37/53* (2013.01); *A61M 39/10* (2013.01); *A61M 2039/1016* (2013.01); *A61M 2039/1066* (2013.01); *A61M 2205/273* (2013.01)

(58) Field of Classification Search
CPC .................. A61M 39/26; A61M 39/18; A61M 2039/1044; A61M 39/10; A61M 39/1055; A61M 2039/1016; A61M 2205/273; F16L 29/04; F16L 37/53; F16L 37/0982
See application file for complete search history.

(56) References Cited

U.S. PATENT DOCUMENTS

| | | | | |
|---|---|---|---|---|
| 2008/0103485 | A1 * | 5/2008 | Kruger | A61M 39/1011 604/533 |
| 2008/0172039 | A1 * | 7/2008 | Raines | A61M 39/1011 604/533 |
| 2014/0265319 | A1 | 9/2014 | Clark et al. | |
| 2015/0119863 | A1 * | 4/2015 | Christensen | A61M 39/10 604/539 |
| 2020/0338330 | A1 | 10/2020 | Shemesh | |
| 2024/0050728 | A1 * | 2/2024 | Jadhav | A61M 39/26 |

FOREIGN PATENT DOCUMENTS

| | | | | |
|---|---|---|---|---|
| FR | 2956327 | A1 * | 8/2011 | A61M 39/1011 |
| WO | WO-2015007650 | A1 * | 1/2015 | A61M 39/10 |
| WO | WO-2017199203 | A1 * | 11/2017 | A61M 39/26 |

* cited by examiner

NON-DISCONNECTING ROTATABLE CONNECTOR ASSEMBLY

FIELD OF THE INVENTION

The present disclosure generally relates to connectors, and, in particular, to a non-disconnecting rotatable connector.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

In some applications, such tubing or catheters may become disconnected due to improper securement and/or when the coupling is subject to forces greater than what the coupling is designed to withstand. Disconnection of tubing or catheters can be dangerous when hazardous drugs are being used. For example, disconnection of tubing used with hazardous drug delivery injections or infusions may result in harm to surrounding individuals.

SUMMARY

One or more embodiments of the present invention are directed to a connector including a housing having a first end and second end opposite the first end, the housing having an interior space, a luer assembly disposed within the interior space of the housing, the luer assembly having a locking ring and the luer assembly configured to couple to a coupling device to secure the coupling device to the connector, and a sleeve at least partially disposed around the luer assembly and disposed within the interior space, the sleeve configured to couple to the locking ring to prevent axial movement of the sleeve relative to the luer assembly and the housing. The housing is rotatable to the luer assembly and the sleeve when the sleeve is coupled to the locking ring to prevent decoupling of the luer assembly from the coupling device when the luer assembly is coupled to the coupling device.

In some embodiments, the luer assembly includes a luer and an end connector. The luer includes a coupling portion configured to couple to the coupling device. The coupling portion includes a first thread configured to engage with a second thread of the coupling device. The luer is coupled to the end connector such that the luer is non-rotatable relative to the end connector.

In some embodiments, the housing includes a housing ring disposed at a first end and the end connector includes a base groove configured to receive and secure the housing ring to prevent axial movement of the luer assembly relative to the housing.

In some embodiments, the luer includes a first channel and the end connector includes a second channel, the first channel being in fluid communication with the second channel when the luer is coupled to the end connector.

In some embodiments, the connector further includes a coupling device configured to couple to the luer assembly. A fluid pathway is formed through the coupling device and the connector when the coupling device is coupled to the luer assembly. The connector has a first configuration and a second configuration, in the first configuration the sleeve is not in contact with the coupling device and in the second configuration the sleeve is in contact with the coupling device. In the second configuration, the coupling device causes the sleeve to axially move towards the second end to cause the sleeve to couple to the locking ring. The coupling device and the luer assembly are rotatable relative to the housing when the connector is in the second configuration to prevent disconnecting of the coupling device from the connector.

In some embodiments, the connector has a first configuration and a second configuration, in the first configuration the sleeve is not coupled to the locking ring and in the second configuration the sleeve is coupled to the locking ring. The sleeve includes a projection and housing includes a slot such that the projection is disposed within the slot when the sleeve is disposed within the interior space. The slot includes a notch and the projection of the sleeve is disposed within the notch when the connector is in the second configuration. The sleeve and the luer assembly are rotatable relative to the housing when the connector is in the second configuration.

In some embodiments, the sleeve includes a groove configured to receive the locking ring to axially fix the sleeve relative to the luer assembly.

In some embodiments, the sleeve axially moves towards the second end relative to the luer assembly to couple the sleeve to the locking ring when the coupling device is coupled to the luer assembly.

One or more embodiments of the present invention are directed to a connector including a housing having a first end and second end opposite the first end, the housing having an interior space, the housing being substantially cylindrical and having a housing ring disposed at the first end, the housing ring extending radially inward into the interior space, a luer assembly disposed within the interior space of the housing, the luer assembly including a luer coupled to an end connector, the luer having coupling portion including a first thread configured to engage with a second thread of a coupling device to couple the coupling device to the luer assembly, the end connector having a base groove configured to receive the housing ring to secure the luer assembly to the housing and the end connector having a locking ring, and a sleeve at least partially disposed around the luer assembly and disposed within the interior space, the sleeve having a groove configured receive the locking ring to secure the luer assembly to the sleeve to prevent axial movement of the sleeve relative to the luer assembly and the housing. The housing is rotatable to the luer assembly and the sleeve, and the sleeve is coupled to the locking ring to prevent decoupling of the luer assembly from the coupling device when the luer assembly is coupled to the coupling device.

One or more embodiments of the present invention are directed to a connector including a housing having a first end and second end opposite the first end, the housing having an interior space, the housing being substantially cylindrical and having a housing ring disposed at the first end and extending radially inward into the interior space, the first end having a diameter greater than a diameter of the second end, a luer assembly disposed within the interior space of the housing, the luer assembly including a luer non-rotatably coupled to an end connector, the luer having coupling portion including a first thread configured to engage with a second thread of a coupling device to couple the coupling device to the luer assembly, the end connector having a base groove configured to receive the housing ring to secure the luer assembly to the housing and the end connector having a locking ring, wherein the luer includes a first channel and the end connector includes a second channel, the first channel being in fluid communication with the second channel when the luer is coupled to the end connector, and a sleeve at least partially disposed around the luer assembly and disposed within the interior space, the sleeve having a groove configured receive the locking ring to secure the luer assembly to the sleeve to prevent axial movement of the sleeve relative to the luer assembly and the housing, the sleeve having a projection configured to engage with a slot of the housing when the sleeve is disposed within the interior space. The connector has a first configuration and a second configuration, in the first configuration the sleeve is not coupled to the locking ring and in the second configuration the sleeve is coupled to the locking ring. The sleeve axially moves towards the second end relative to the luer assembly to couple the sleeve to the locking ring when the coupling device is coupled to the luer assembly. The housing is rotatable to the luer assembly and the sleeve, and the sleeve is coupled to the locking ring to prevent decoupling of the luer assembly from the coupling device when the connector is the second configuration. A fluid pathway is formed through the coupling device and the connector when the connector is the second configuration.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1A:
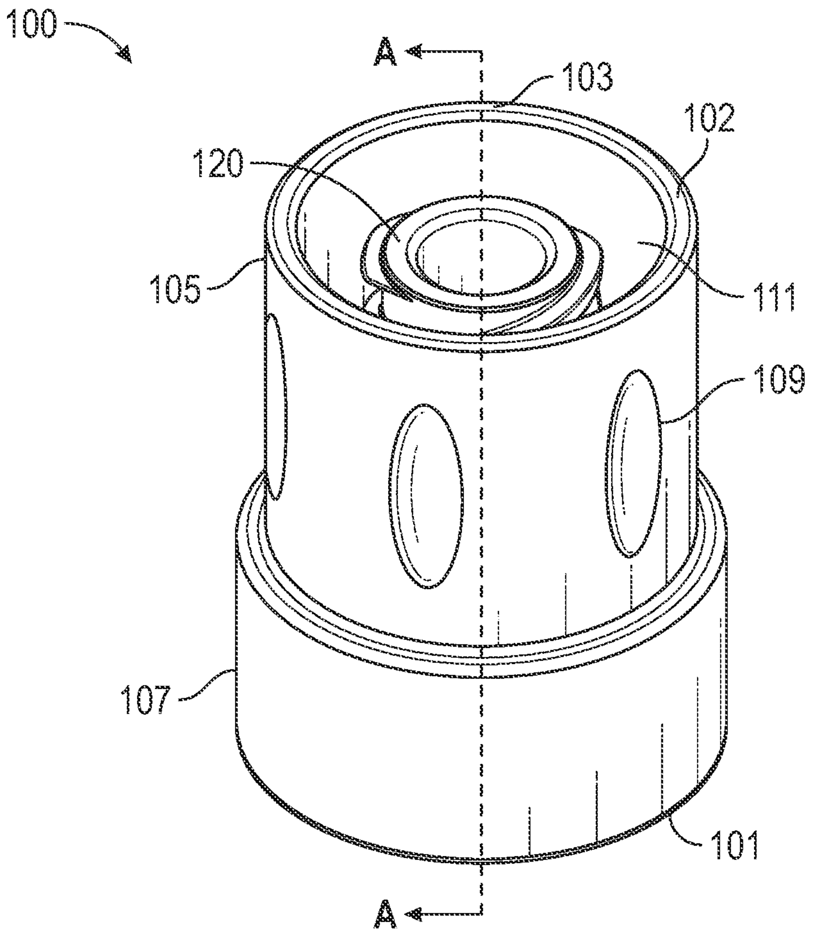
FIG. 1A is a front perspective view of a connector in accordance with various aspects of the present disclosure.

The disclosed connector includes a cover and a luer configured to couple to a coupling device. The connector may have a first configuration and a second configuration. In the first configuration, the connector is not coupled to the coupling device. In the second configuration, the connector is coupled to the coupling device.

The connector may be configured to couple a first portion of tubing to a second portion of tubing. For example, the first portion of tubing may be coupled to the connector and the second portion of tubing may be coupled to the coupling device. The first portion of tubing and/or the second portion of tubing may also couple to a patient or fluid source. In some embodiments, the connector allows for the flow of fluid from the first portion of tubing to the second portion of tubing. For example, when the connector is coupled to the coupling device, a fluid pathway may be formed through the connector and the coupling device to allow the flow of fluid from the first portion of tubing through the connector and the coupling device to the second portion of tubing. The fluid pathway may allow for the flow of fluid from the second portion of tubing through the coupling device and the connector to the first portion of tubing. In some embodiments, the second portion of tubing is coupled to a syringe. The second portion of tubing may be a syringe containing a medicament or drug.

In some embodiments, the coupling device is configured to remain coupled to the connector even upon the application of a force. For example, when the coupling device is coupled to the connector, a pullout force may be applied to a portion of tubing or syringe coupled to the coupling device. The connector may remain coupled to the coupling device in response to the pullout force to prevent the connector from decoupling from the coupling device. The pullout force may be a force that occurs along the longitudinal axis of the coupling device and/or the connector. In some embodiments, the pullout force is caused by tugging or pulling on the second portion of tubing or the syringe coupled to the coupling device. Alternatively, the pullout out force applied to the coupling device may be caused by tugging or pulling on the connector and/or the first portion of tubing coupled to the connector.

In some embodiments, the second portion of tubing and/or the syringe may contain hazardous materials, such as hazardous drugs. Connector being configured to prevent decoupling results in the prevention of leakage or spilling of the hazardous drugs. The hazardous may be harmful to surrounding individuals if exposed and/or not contained in the proper containers, vessels, or delivery devices. Connector remaining coupled to coupling device in response to pullout force prevents exposure of the hazardous drugs to surrounding individuals.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the connection of medical fittings for the administration of medical fluid using the disclosed connector, it is to be understood that this description is only an example of usage and does not limit the scope of the claims. Various aspects of the disclosed connector may be used in any application where it is desirable to secure the connection of various tubing and fittings.

The disclosed connector overcomes several challenges discovered with respect to certain conventional couplers. One challenge with certain conventional couplers is that certain conventional couplers may be easily decoupled. For example, certain conventional couplers may release in response to pullout forces experienced during patients rolling over in bed, patients catching tubing or lines on bed rails, moving patients to a different bed, fidgeting by pediatric patients, and/or disoriented adult patients pulling out their lines. Indeed, the Association for Vascular Access (AVA) Annual Scientific Meeting in 2017 reported a 10% dislodgement rate for 1,000 patients fitted with peripheral IV catheters, translating to approximately 33 million dislodgements per year in the U.S. alone. Because the accidental or unintentional dislodgement of tubing, catheters, or fittings may interrupt the administration of medical fluids, the use of certain conventional couplers is undesirable.

Therefore, in accordance with the present disclosure, it is advantageous to provide couplers and coupler/connector assemblies as described herein that prevent disconnection in response to a pullout force. The disclosed couplers and coupler/connector assemblies are structured as described herein so as to permit the secure retention of the connectors to coupling devices in response to a pullout force.

Figure 1B:
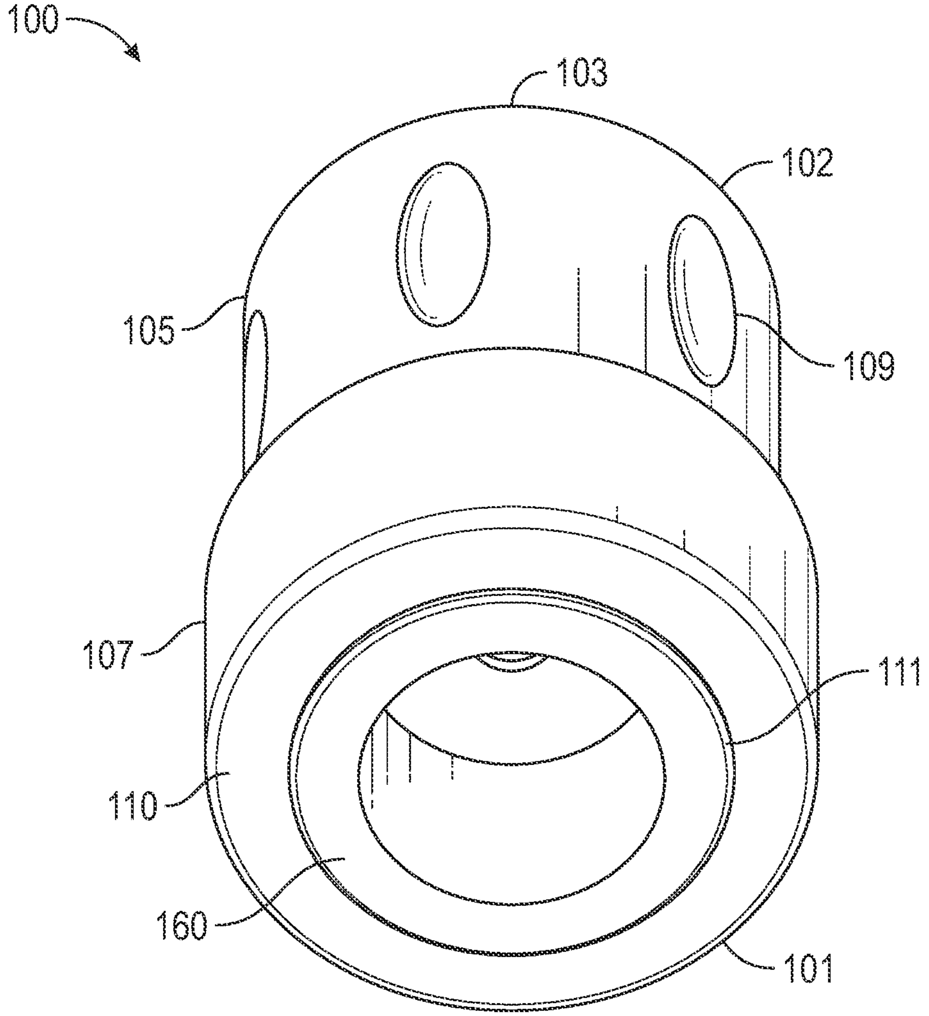
FIG. 1B is a bottom perspective view of the connector of FIG. 1A.

FIG. 1A is a front perspective view of a connector in accordance with various aspects of the present disclosure. FIG. 1B is a bottom perspective view of the connector of FIG. 1A.

With reference to FIGS. 1A-1B, connector 100 allows the flow of a fluid, such as a medical fluid, from a fluid source (e.g., syringe or tubing) to patient end by coupling a portion of tubing or syringe with another portion of tubing or line in fluid communication. Connector 100 may be configured to couple to a coupling device (e.g., coupling device 200), which may be coupled to a fluid source housing, for example, hazardous drugs.

In some embodiments, connector 100 includes central axis A-A and connector 100 and a coupling device are coupled in series along central axis A-A. Central axis A-A may extend longitudinally along the length of connector 100. Connector 100 may have a first configuration and a second configuration. In the first configuration, connector 100 is decoupled from a coupling device. In the second configuration, connector 100 is coupled to a coupling device. Connector 100 may be coupled to a coupling device such that central axis A-A extends through connector 100 and the coupling device.

In some embodiments, connector 100 is coupled to a first portion of tubing to allow the first portion of tubing to be connected to a coupling device. Connector 100 may include first end 101 and second end 103. First end 101 may be coupled to tubing (e.g., a first portion of tubing), one or more connectors, and/or bonded with a syringe, and second end 103 may be configured to receive a coupling device. In some embodiments, a portion of tubing can be coupled with, or engage with first end 101 of connector 100. Connector 100 via first end 101 may be in fluid communication with the tubing to allow fluid to pass through connector 100. In some embodiments, first end 101 can have a flat surface to allow for clinicians to easily clean and disinfect first end 101. First end 101 may be in fluid connection with second end 103. First end 101 and second end 103 may be disposed along the longitudinal length of connector 100. For example, first end 101 and second 103 may be disposed along central axis A-A. First end 101 and/or second end 103 may include an opening to allow first end 101 and/or second end 103 to be in fluid communication with one or more elements (e.g., tubing, connectors, valves, collars, attachments, syringes etc.). For example, first end 101 may be coupled to a tube and second end 103 may include an opening to allow for fluid communication through connector 100.

In some embodiments, fluid can exit or flow through connector 100 via second end 103 disposed opposite to first end 101. The flow path through connector 100 can have a straight fluid pathway to make flushing easier and to reduce the risk of hemolysis. Optionally, connector 100 can include features (e.g., raised features, gripping features) disposed on the outer surface of connector 100 to allow a clinician to more easily handle or manipulate connector 100. Some embodiments of connector 100 may provide connectors that are compatible with connectors of other portions of fluid delivery systems. Connector 100 may be substantially cylindrically shaped.

In some embodiments, connector 100 includes housing 102. Housing 102 may be substantially cylindrically shaped and may include tubing portion 107 and mating portion 105. Tubing portion 107 may be proximate first end 101 and mating portion 105 may be disposed proximate second end 103. Tubing portion 107 may house include end connector 160, which may be configured to couple to a portion of tubing allowing connector 100 to be in fluid communication with the portion of tubing.

In some embodiments, mating portion 105 is disposed opposite tubing portion 107 and a coupling device is configured to be at least partially disposed within mating portion 105 to secure connector 100 to a coupling device. For example, mating portion 105 may include luer 120 configured to couple to a coupling device (e.g., coupling device 200) to secure the coupling device to connector 100, as described below. Luer 120 may be at least partially disposed within mating portion 105 proximate second end 103. In some embodiments, luer 120 is configured to couple and engage with a portion of the coupling device to secure the coupling device to connector 100. Luer 120 may be disposed within housing 102 such that a portion of housing 102 (e.g., mating portion 105) is circumferentially disposed around luer 120. Groove 109 may be continuously circumferentially disposed around mating portion 105.

Housing 102 may be substantially cylindrical and may be configured to house luer 120. In some embodiments, when luer 120 is coupled to a coupling device, the coupling device is at least partially disposed within housing 102. Housing 102 may include grooves 109 circumferentially disposed around housing 102, such as around mating portion 105.

Grooves 109 may be configured to assist a user in rotating housing 102. In some embodiments, tubing portion 107 has a maximum diameter greater than mating portion 105. For example, housing 102 may taper from first end 101 to second 103. In some embodiments, tubing portion 107, and mating portion 105 form a unitary structure that comprises housing 102.

In some embodiments, housing 102 is configured to receive and house end connector 160. End connector 160 may be at least partially disposed within tubing portion 107. End connector 160 may be disposed proximate first end 101 compared to second end 103. Housing 102 may include housing ring or ring 110 at first end 101. Ring 110 may extend radially inward from housing 102. In some embodiments, ring 110 is one or more projections circumferentially disposed along an interior surface of housing 102 and extending radially inward. In some embodiments, ring 110 extends radially inward towards central axis A-A. Housing 102 may be hollow such that housing 102 can receive and house one or more components. For example housing 102 may include interior space 111 and ring 110 may extend radially inward into interior space 111. In some embodiments, ring 110 extends perpendicularly towards central axis A-A.

In some embodiments, a second portion of tubing is terminated by coupling device (e.g., coupling device 200) to allow the second portion of tubing to be connected and/or disconnected from connector 100. In some embodiments, housing 102 includes features and/or components (e.g., luer 120) that allow connector 100 to couple to a coupling device. The coupling device (e.g., coupling device 200) may be coupled to a syringe or to a fluid source via tubing. In some embodiments, the syringe or fluid source coupled to the coupling device includes hazardous drugs. The hazardous drugs may be harmful for individuals if exposed. Connector 100 may be configured to remain connected to the coupling device in response to a pullout force to prevent decoupling and exposure of the hazard drugs.

As can be appreciated, connector 100 and the coupling device (e.g., coupling device 200) can be coupled and decoupled to permit fluid communication as desired. Connector 100 may couple with coupling device 200 to provide needle free connections. Advantageously, connector 100 may pair with coupling device 200 to form a leak-free closed system, allowing the delivery of various drugs or fluids.

Figure 2:
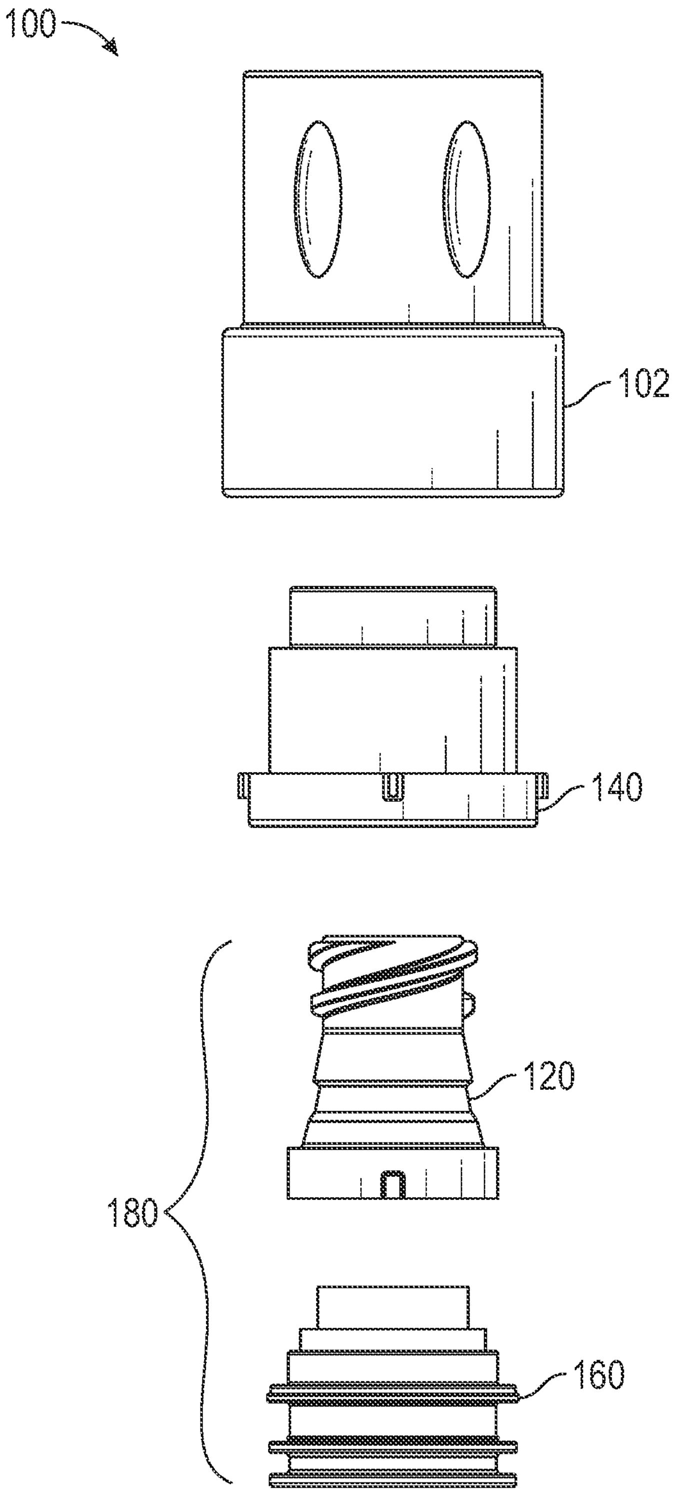
FIG. 2 is an exploded view of the connector of FIG. 1A showing a housing, a luer, a sleeve, and an end connector in accordance with various aspects of the present disclosure.
Figure 3:
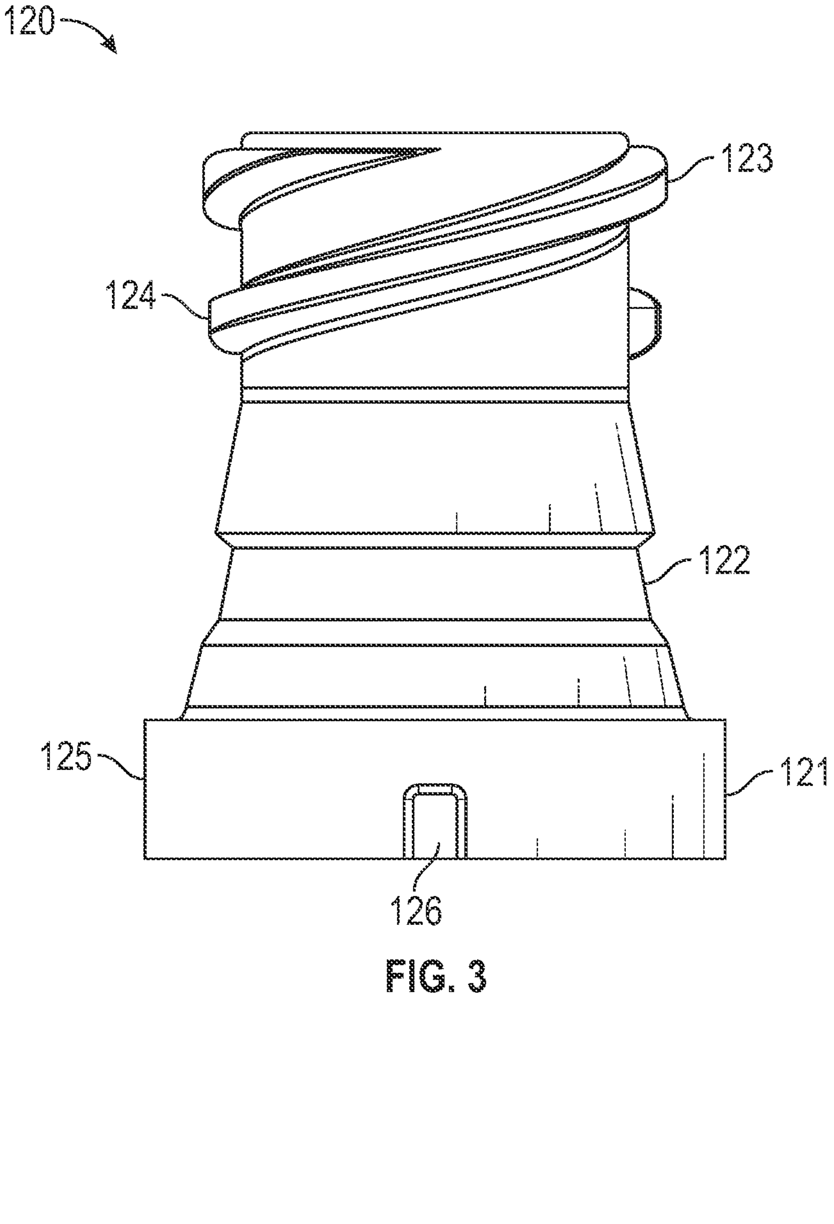
FIG. 3 is a front view of the luer of FIG. 2 in accordance with various aspects of the present disclosure.
Figure 4:
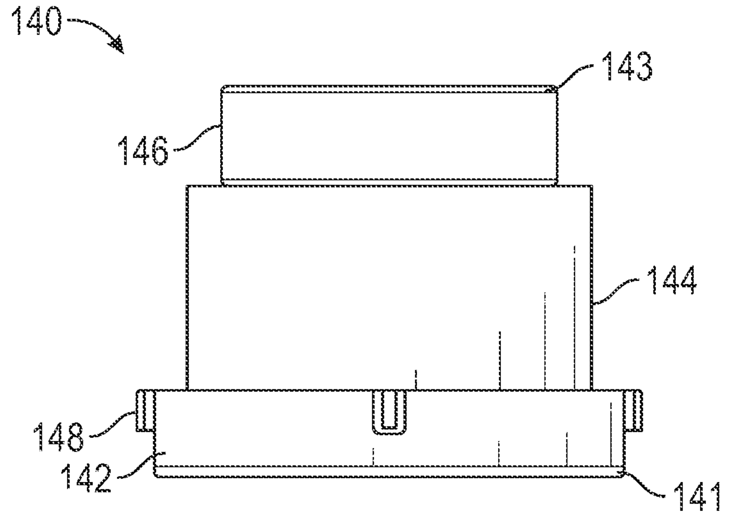
FIG. 4 is a front view of the sleeve of FIG. 2 in accordance with various aspects of the present disclosure.
Figure 5:
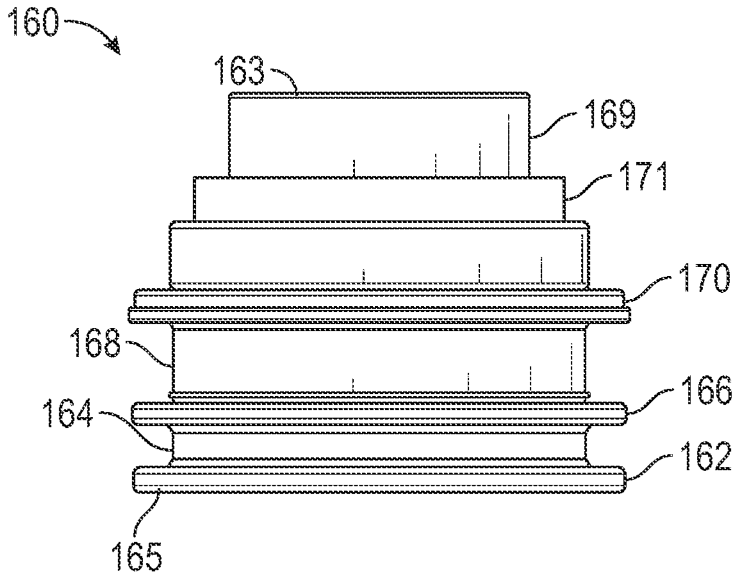
FIG. 5 is a front view of the end connector of FIG. 2 in accordance with various aspects of the present disclosure.

FIG. 2 is an exploded view of the connector of FIG. 1A showing a housing, a luer, a sleeve, and an end connector in accordance with various aspects of the present disclosure. FIG. 3 is a front view of the luer of FIG. 2 in accordance with various aspects of the present disclosure. FIG. 4 is a front view of the sleeve of FIG. 2 in accordance with various aspects of the present disclosure. FIG. 5 is a front view of the end connector of FIG. 2 in accordance with various aspects of the present disclosure.

With reference to FIGS. 2-5, connector 100 may include housing 102, sleeve 140 and luer assembly 180. Luer assembly 180 includes luer 120 and end connector 160. Housing 102 may be configured to house luer assembly 180 and sleeve 140. For example, luer assembly 180 and sleeve 140 may be disposed within housing 102. Luer assembly 180 may be configured to be disposed at least partially within sleeve 140 such that sleeve 140 circumferentially surrounds luer assembly 180. In some embodiments, luer assembly 180 includes a channel to allow for a fluid pathway through luer assembly 180. For example, luer 120 and end connector 160 each may include a channel that are in fluid communication to allow for a fluid pathway through luer assembly 180.

In some embodiments, luer 120, sleeve 140, and end connector 160 are disposed within housing 102. For example, luer 120, sleeve 140, and end connector 160 may be disposed within interior space 111 of housing 102. Luer 120 may configured to be disposed within sleeve 140. In some embodiments, sleeve 140 is circumferentially disposed around luer 120 such that sleeve 140 surrounds luer 120. End connector 160 may be disposed within sleeve 140. In some embodiments, end connector 160 is disposed at least partially within sleeve 140 and sleeve 140 is disposed within housing 102. Luer 120, sleeve 140, and end connector 160 may be coupled in series along central axis A-A. In some embodiments, luer 120, sleeve 140, and end connector 160 are coupled together and disposed within housing 102 such that central axis A-A bifurcates each of housing 102, luer 120, sleeve 140, and end connector 160.

With reference to FIG. 3, Connector 100 may include luer 120 disposed within housing 102. Luer 120 may include first end 121 and second end 123. First end 121 may be disposed opposite second end 123. Luer 120 may include coupling portion 124 disposed at second end 123. In some embodiments, coupling portion 124 includes threads to couple to a coupling device. Alternatively, coupling portion 124 may couple to the coupling device via friction fitting, fasteners, magnets, or other coupling mechanisms. Luer 120 may include groove 122 disposed proximate first end 121 and base 125. Groove 122 may be disposed between coupling portion 124 and base 125.

In some embodiments, base 125 has a greater diameter than coupling portion 124, which has a greater diameter than groove 122. In some embodiments, coupling portion 124 is tapered. Luer 120 may taper form first end 121 to second end 123. Luer 120 may be disposed within housing 102 such that first second end 123 is disposed proximate second end 103. In some embodiments, the entirety of luer 120 is disposed within housing 102. In some embodiments, luer 120 includes one or more slots 126. Slot 126 may be disposed on base 125. In some embodiments, one or more slots 126 are disposed on base 125 and configured to receive on or more projections (e.g., projections 154) of sleeve 140.

With reference to FIG. 4, connector 100 may include sleeve 140, which may be configured to receive luer 120. Sleeve 140 may include first end 141 and second end 143, which may be opposite first end 141. Sleeve 140 may taper from first end 141 to second end 143. Sleeve 140 may include sleeve base 142 disposed at first end 141. Sleeve base 142 may include projections 148 circumferentially disposed along the external surface of sleeve base 142. In some embodiments, sleeve base 142 includes a plurality of projections 148 equidistantly spaced apart along sleeve base 142. Sleeve base 142 may include one, two, three, four, or greater than four projections 148. Projections 148 may be configured to engage with one or more slots disposed on the interior surface of housing 102. For example, housing 102 may include one or more slots (e.g., slots 113) configured to receive corresponding projections 148.

Sleeve 140 may include middle portion 144 and top portion 146. Middle portion 144 may be disposed between sleeve base 142 and top portion 146. In some embodiments, sleeve base 142 has a diameter greater than middle portion 144. Middle portion 144 may have a diameter greater than top portion 146.

In some embodiments, sleeve 140 receives luer 120 such that first end 121 of luer 120 is disposed proximate first end 141 of sleeve 140. Luer 120 may be inserted through sleeve base 142 and extend through middle portion 144 and out of top portion 146 at first end 143. In some embodiments, when luer 120 is disposed within sleeve 140, first end 121 of luer 120 is disposed within middle portion 144 of sleeve 140 and coupling portion 124 extends through and out of second end 143.

With reference to FIG. 5, connector 100 may include end connector 160. End connector 160 may include first end 161 and second end 163 disposed opposite first end 161. End connector 160 may include connector base 165, ring 166, and locking ring 170, and grooves 164 and 168. Groove 164 may be a base groove configured to receive housing ring 110. In some embodiments, groove 164 is disposed between connector base 165 and ring 166, and groove 168 is disposed between ring 166 and locking ring 170. Ring 166 may be disposed between connector base 165 and locking ring 170. In some embodiments, ring 166 and locking ring 170 are one or more projections circumferentially disposed along an exterior surface of end connector 160 and extending radially outward.

Connector base 165 and rings 166 and 170 may extend radially outward from end connector 160 and may circumferentially surround end connector 160. In some embodiments, each of connector base 165 and rings 166 and 170 have a diameter greater than grooves 164 and 168. Groove 168 may have a height greater than the height of groove 164. End connector 160 may include top portion 169 disposed at second end 163. In some embodiments, end connector 160 tapers from locking ring 170 to second end 163. End connector 160 may taper from first end 161 to second end 163.

Figure 6A:
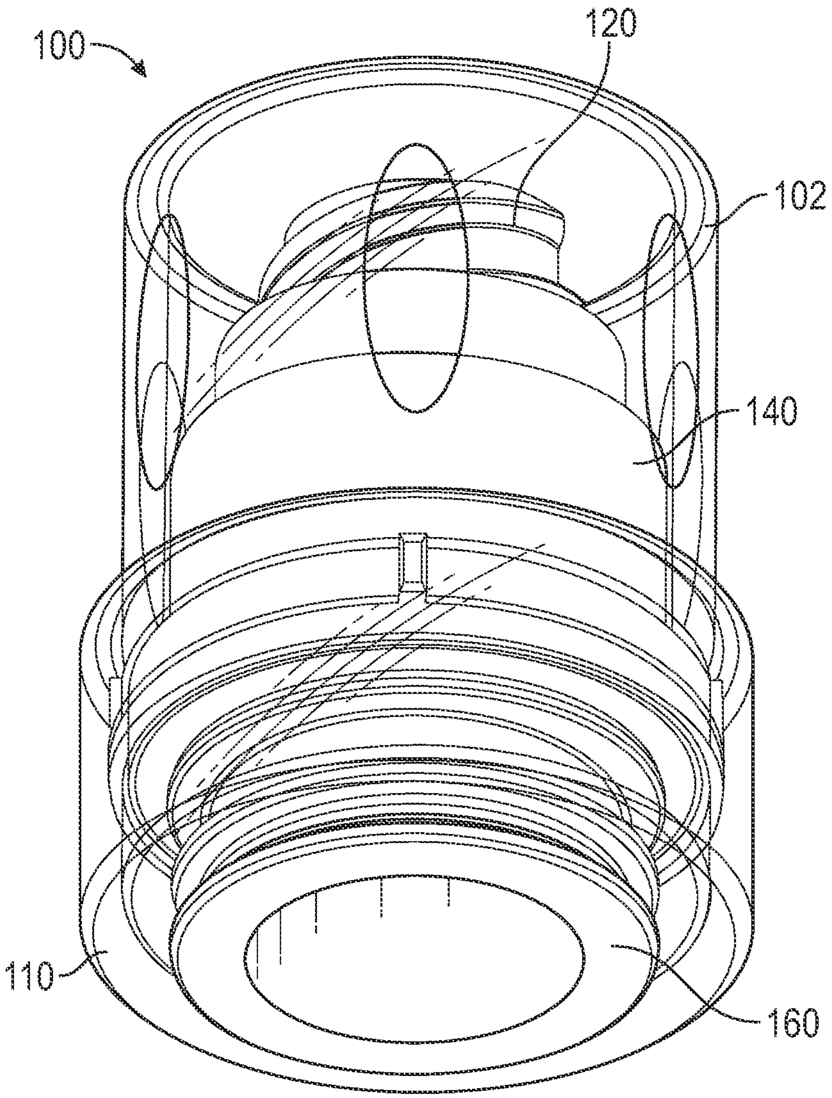
FIG. 6A is a bottom perspective view of the connector of FIG. 1A with the cover being transparent in accordance with various aspects of the present disclosure.
Figure 6B:
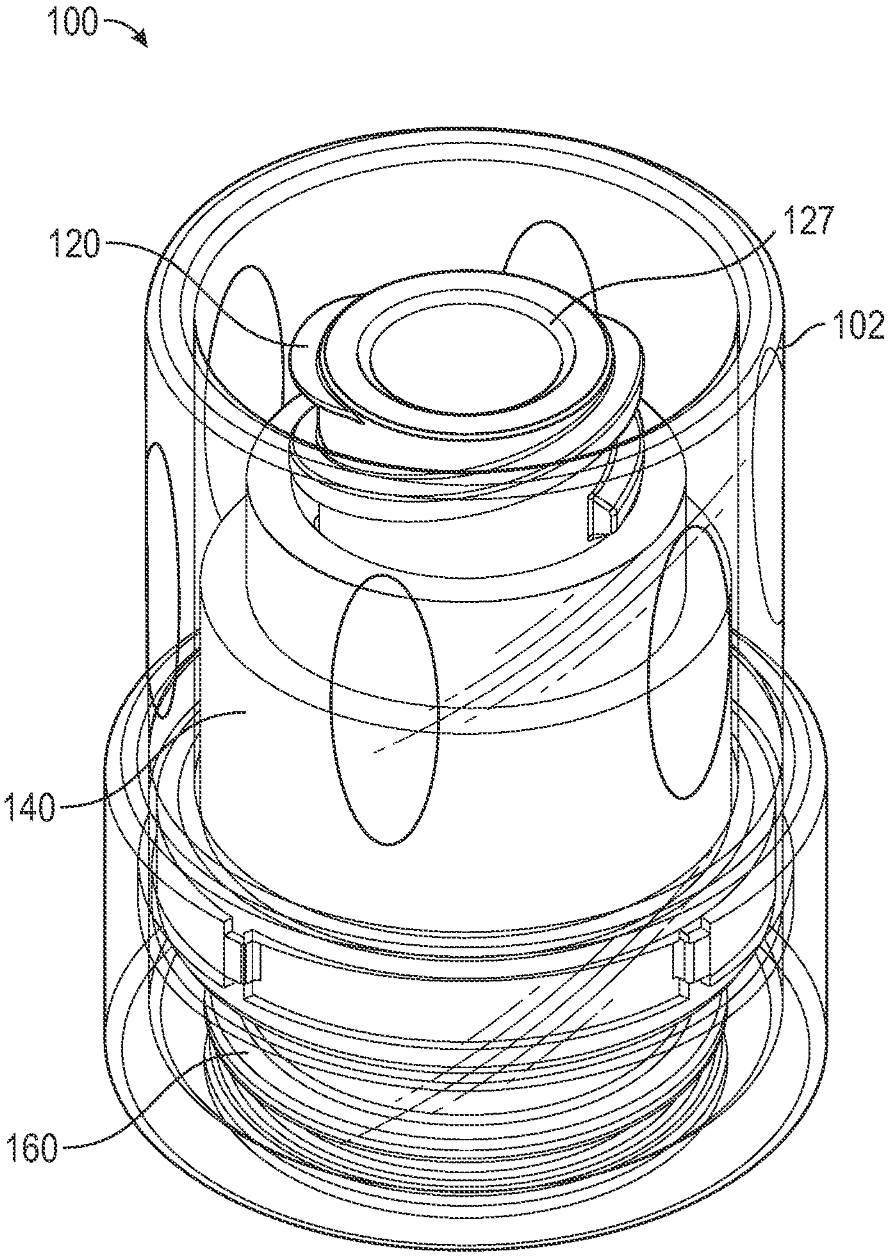
FIG. 6B is a front perspective view of the connector of FIG. 6A in accordance with various aspects of the present disclosure.
Figure 7A:
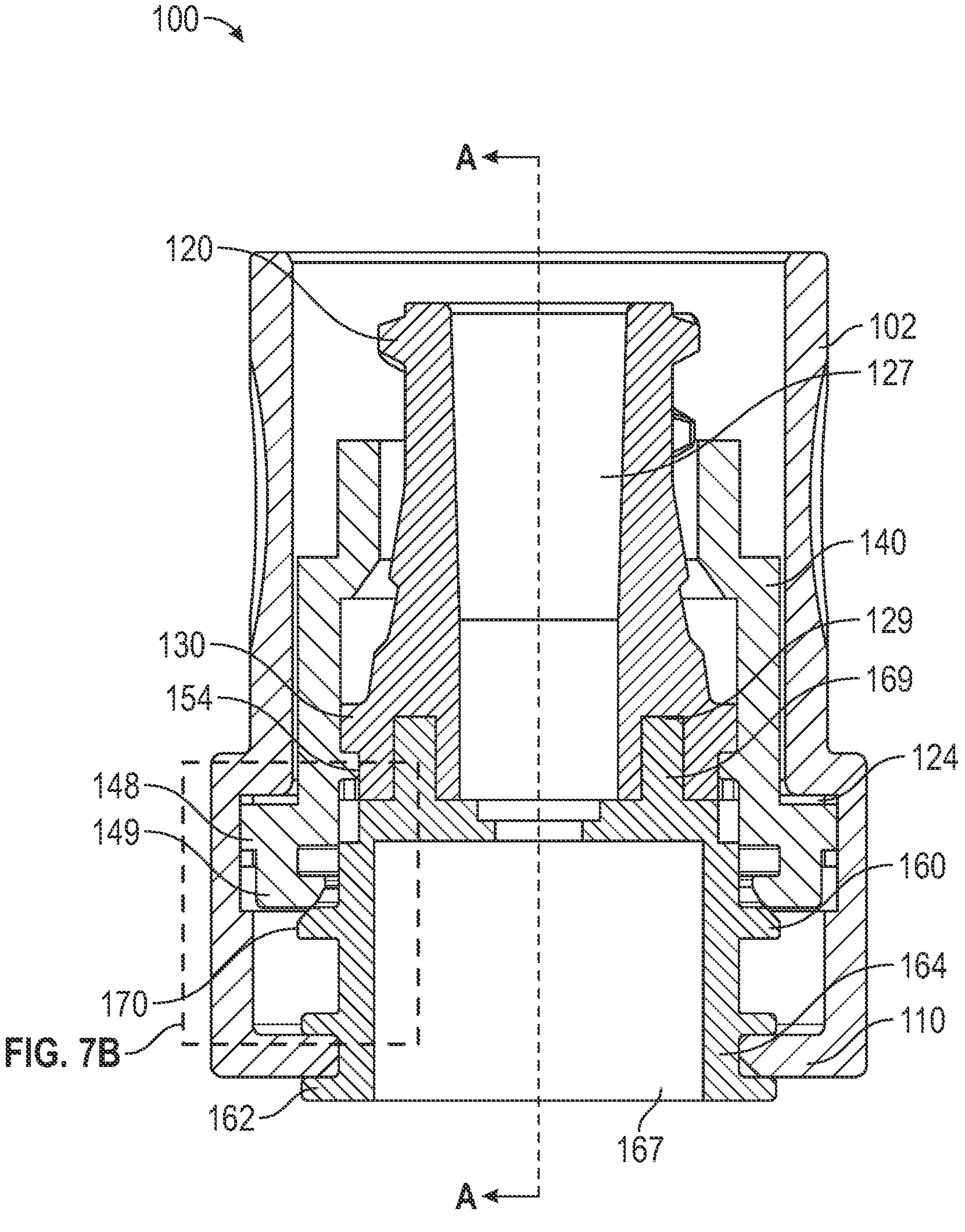
FIG. 7A is a cross-sectional view of the connector of FIG. 1A in accordance with various aspects of the present disclosure.
Figure 7B:
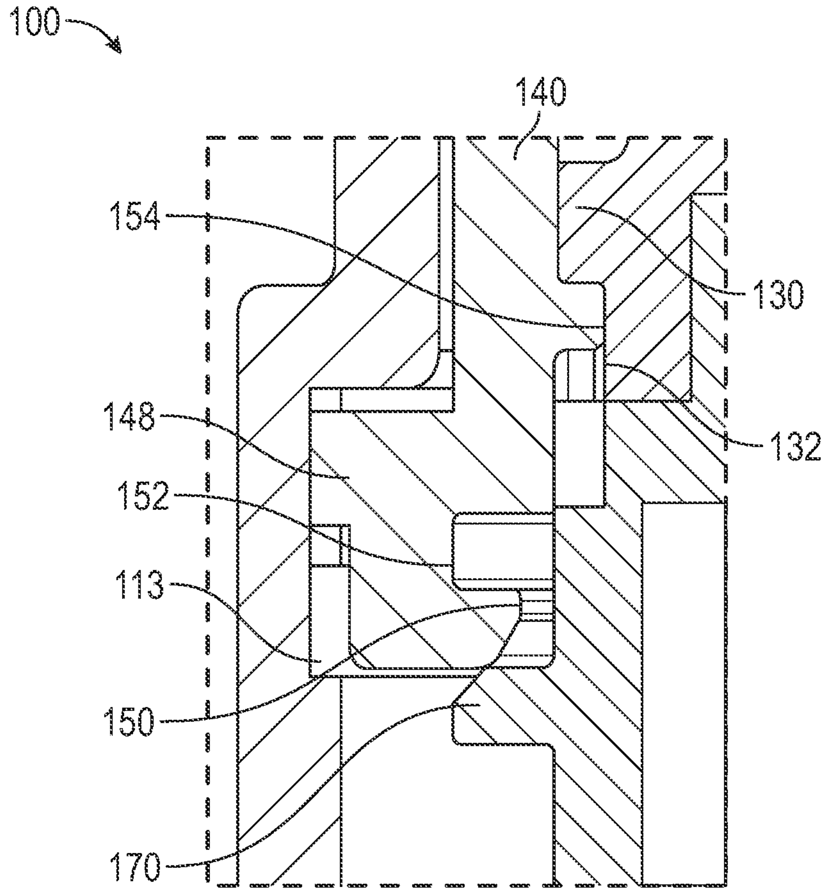
FIG. 7B is a zoomed in view of the connector of FIG. 7A in accordance with various aspects of the present disclosure.
Figure 7C:
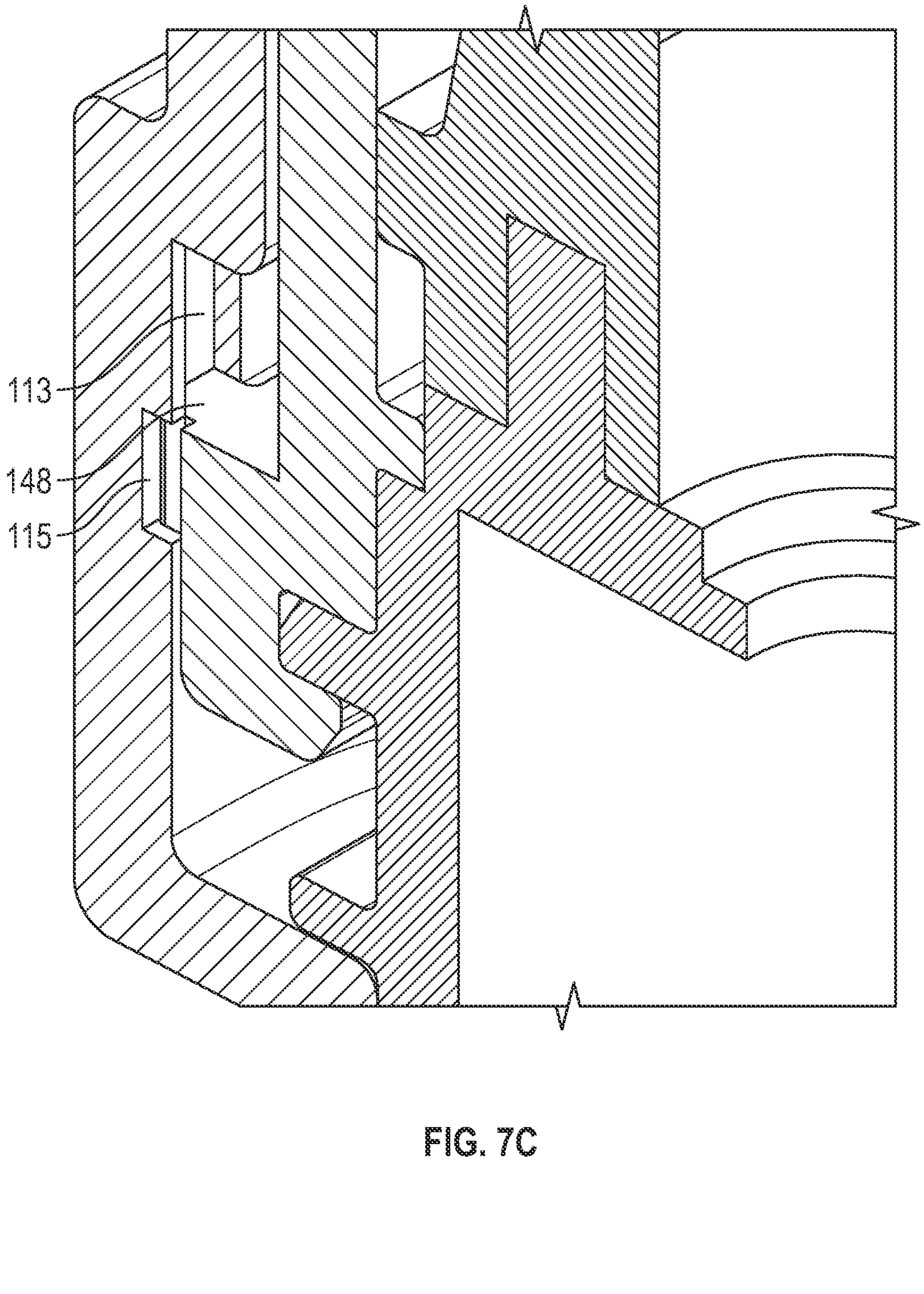
FIG. 7C is a zoomed in cross-sectional perspective view of the connector of FIG. 1A with sleeve secured to the end connector and rotatable relative the housing in accordance with various aspects of the present disclosure.

FIG. 6A is a bottom perspective view of the connector of FIG. 1A with the cover being transparent in accordance with various aspects of the present disclosure. FIG. 6B is a front perspective view of the connector of FIG. 6A in accordance with various aspects of the present disclosure. FIG. 7A is a cross-sectional view of the connector of FIG. 1 in accordance with various aspects of the present disclosure. FIG. 7B is a zoomed in view of the connector of FIG. 7A in accordance with various aspects of the present disclosure. FIG. 7C is a zoomed in cross-sectional perspective view of the connector of FIG. 1A with sleeve secured to the end connector and rotatable relative the housing in accordance with various aspects of the present disclosure.

In some embodiments, luer 120 includes channel 127 and end connector 160 includes channel 167. Channel 127 and channel 167 may be disposed along central axis A-A and may be in fluid communication with each other. Channel 127 may extend through luer 120 to allow fluid to flow through luer 120. In some embodiments, channel 127 and channel 167 form a fluid pathway through luer assembly 180 and connector 100. When a coupling device (e.g., coupling device 200) is coupled to connector 100, a portion of the coupling device may be disposed within channel 127 to form an air tight or water tight pathway between the coupling device and connector 100. Channel 167 may be configured to be in fluid communication with a tubing, such as an IV tubing. For example, end connector 160 may be configured to couple to or be integrated with a fluid connection system, such as a tubing, to allow for fluid transfer through connector 100 to a patient.

With reference to FIGS. 6A-7C, luer 120 may be disposed within sleeve 140, which may be coupled to end connector 160 and disposed within housing 102. In some embodiments, luer 120 is inserted through sleeve 140 and end connector 160 is coupled to luer 120 at first end 121. Once coupled together, luer 120, sleeve 140, and end connector 160 may be inserted into house 102 such that ring 110 of housing 102 is disposed within groove 164 of end connector.

In some embodiments, housing 102 includes one or more slots 113 proximate where tubing portion 107 and mating portion 105 meet or are joined. Slots 113 may be disposed on an inner or interior surface of housing 102 and may be where housing 102 reduces in diameter. In some embodiments, when luer 120 is disposed in sleeve 140 and coupled to end connector 160, and disposed within housing 102, sleeve base 142 is disposed proximate slots 113 such that projections 148 engage with and are disposed within slots 113 to prevent further axial of movement of sleeve 140 toward second end 123. Luer 120 being coupled to end connector 160 may form luer assembly 180, which may be disposed within sleeve 140.

In some embodiments, luer assembly 180 and sleeve 140 are disposed and secured within housing 102 due to ring 110 being disposed within groove 164. For example, luer assembly 180 may be disposed within sleeve 140 and ring 110 of housing 102 may be configured to deflect or flex and may flex during insertion of luer assembly 180 into housing 102. Ring 110 may deflect or flex as luer assembly 180 moves axially towards first end 103. Due to luer assembly 180 being disposed within sleeve 140, luer assembly 180 and sleeve 140 may axially move towards second end 103 until projections 148 of sleeve base 142 contact or engage with slots 113. Projections 148 may be disposed within slots 113 to prevent further axial movement of sleeve 140 towards first end 101.

Projections 148 engaging with and/or being disposed within slots 113 may occur simultaneously with ring 110 being disposed within groove 164. Projections 148 being disposed within corresponding slots 113 prevents axial movement of sleeve 140 towards second end 103 of housing 102 and ring 110 being disposed within groove 164 prevents axial movement of end connector 160 and luer 120 relative to housing 102. In some embodiments, ring 110 being disposed within groove 164 allows housing 102 to rotate relative to end connector 160. Housing 102 may include a number of slots 113 corresponding to the number of projections 148 of sleeve 140.

In some embodiments, sleeve 140 is axially movable relative to luer 120, end connector 160, and housing 102. For example, when luer assembly 180 and sleeve 140 are disposed and secured within housing 102, luer assembly 180 may be fixed (e.g., non-movable) relative to housing 102, and sleeve 140 may be axially movable relative to housing 102 and luer assembly 180.

In some embodiments, luer 120 is coupled to end connector 160 to form luer assembly 180. For example, luer 120 may include recessed groove 129 configured to receive top portion 169 of end connector 160. Luer 120 may be fixedly coupled to top portion 169 of end connector 160 such that luer 120 and end connector 160 form a unitary structure. In some embodiments, luer 120 (e.g., groove 129) is solvent bonded to top portion 169 such that luer 120 is fixedly coupled to end connector 160. Alternatively, luer 120 may be fixedly coupled to end connector 160 using magnets, fasteners, adhesives, screws, or any other coupling mechanism.

In some embodiments, sleeve 140 includes projections 154 extending radially inward from an inner surface of sleeve 140. In some embodiments, projections 154 are ribbed projections. Projections 154 may be a ring circumferentially disposed along the inner surface of sleeve 140 and may be configured to extend radially inward. Luer 120 may include one or more slots 132, and projections 154 may be configured to engage with slot 132. For example, sleeve 140 may slide over luer 120 from second end 123 to first end 121. In some embodiments, slot 132 is formed due to a recessed portion of luer 120 aligning with recessed edge 171 of end connector 160. In other words, a portion of luer 120 and a portion of end connector 160 may form slot 132. In some embodiments, sleeve 140 is inserted into housing 102 such that projections 148 are disposed within or proximate slot 113 to prevent axially movement of sleeve 140 towards second end 103 of housing 102 relative to housing 102.

In some embodiments, luer assembly 180 is configured to couple to a coupling device (e.g., coupling device 200). For example, a coupling device may be configured to engage with luer 120 (e.g., coupling portion 124) to secure the coupling device to luer assembly 180. The coupling device may couple with luer assembly 180 such that the coupling device is not removable from luer assembly 180 due to a pullout force. In some embodiment, when the coupling device is coupled to luer assembly 180, the coupling device is at least partially disposed in housing 102 due to coupling portion 124 being disposed within housing 102.

In some embodiments, luer 120 is coupled to end connector 160 such that luer 120 is axially fixed in place relative to end connector 160. As discussed above, top portion 169 may be disposed within recessed groove 129 such that end connector 160 is coupled to luer 120. Luer 120 may be coupled to end connector 160, which may be coupled to housing 102. For example, ring 110 of housing 102 may be disposed within groove 164 to secure end connector 160 to housing 102. Ring 110 of housing 102 being disposed within groove 164 results in end connector 160 being fixed relative to housing 102. In some embodiments, luer 120 being coupled to end connector 160, and end connector 160 being coupled to housing 102 results in luer 120 being axially fixed relative to end connector 160 and housing 102.

Luer assembly 180 may be at least partially disposed within sleeve 140. Sleeve 140 may be axially moveable relative to luer assembly 180. Sleeve 140 may also be movable relative to housing 102. Sleeve 140 may be configured to move towards first end 101 and second end 103 of housing 102 relative to luer assembly 180 and housing 102. In some embodiments, coupling of the coupling device to luer assembly 180 results in axial movement of sleeve 140 relative to housing 102 and luer assembly 180.

In some embodiments, coupling portion 124 includes threads, such as female threads, configured to engage with threads, such as male threads, of the coupling device to secure the coupling device to luer 120 of luer assembly 180. In some embodiments, coupling of the coupling device to luer 120 results in sleeve 140 axially moving towards first end 101 of housing 102. For example, the coupling device may threadably engage with coupling portion 124 and rotate down luer 120 towards first end 101 such that the coupling device is axially rotated/screwed onto coupling portion 124 of luer 120.

With reference to FIGS. 7A-7C, as the coupling device (e.g., coupling device 200) axially rotates down luer 120 via coupling portion 124, the coupling device may contact sleeve 140. Further rotation of the coupling device results in the coupling device axially moving towards first end 101 and axially pushing sleeve 140 towards first end 101. Sleeve 140 may slide down or axially move towards first end 101 relative to luer assembly 180 such that locking ring 170 of end connector 160 engages with and is disposed in groove 152 of sleeve 140. Groove 152 of sleeve 140 may be a recessed groove disposed on an inner surface of sleeve base 142. For example, groove 152 may be circumferentially disposed along an inner surface of sleeve base 142.

In some embodiments, locking ring 170 is configured to bend or flex such that when sleeve 140 is pushed against locking ring 170, locking ring 170 flexes. For example, sleeve 140 may exert a force or pressure on locking ring 170 as sleeve 140 axially moves towards first end 101 of housing 102. Locking ring 170 may flex or deflect to allow locking ring 170 to be disposed within groove 152. Locking ring 170 may be configured to flex or deflect until the pressure or force form sleeve 140 is removed to allow locking ring 170 to be disposed within groove 152. When locking ring 170 is disposed within groove 152 of sleeve 140, sleeve 140 may be axially fixed relative to luer assembly 180. In other words, locking ring 170 disposed within groove 152 results in sleeve 140 being secured to end connector 160, which is secured to luer 120 and housing 102.

In some embodiments, locking ring 170 is shaped to allow sleeve 140 to move past locking ring 170 towards first end 101, but not in the opposite direction. Groove 152 may include edge 149. Locking ring 170 may be circumferentially beveled and edge 149 of sleeve 140 may be circumferentially beveled to allow locking ring 170 to move past edge 149 when sleeve 140 moves towards first end 101. Locking ring 170 and edge 149 may be beveled to allow sleeve 140 to move towards first end 101 to allow locking ring 170 to be disposed within groove 152, but prevent sleeve 140 from moving towards second end 103 to allow locking ring 170 to be removed from groove 152. In other words, locking ring 170 and groove 152 may be sized and shaped to allow axially movement of sleeve 140 towards first end 101 to cause locking ring 170 to be disposed within groove 152.

Upon locking ring 170 being disposed within groove 152, sleeve 140 may be axially fixed relative to end connector 160 and luer 120. For example, once locking ring 170 is disposed within groove 152, sleeve 140 may be prevented from axially moving towards first end 101 or second end 103. Sleeve 140 may move axially towards first end 101 to cause locking ring 170 to be disposed within groove 152 due to a coupling device (e.g., coupling device 200) pushing sleeve 140 axially towards first end 101. This results in locking ring 170 being disposed within groove 152. In some embodiments, the coupling device being completely coupled to luer 120 results in locking ring 170 being disposed within groove 152.

With reference to FIGS. 7B-7C, sleeve 140 moving axially down towards first end 101 results in locking ring 170 being disposed within groove 152, projection 148 moving axially down within slot 132 towards first end 101, and projection 154 moving axially down within slot 113 towards first end 101. Projection 148 moving axially down within slot 132 towards first end 101 and projection 154 moving axially down within slot 113 towards first end 101 results in sleeve 140 and luer assembly 180 being rotatable relative to housing 102. Housing 102 may include notch 115. Notch 115 may be disposed adjacent to slot 113 towards first end 101 compared to second end 103. Notch 115 may extend partially along slot 113 and may allow for projection 148 to enter and exit slot 113. In some embodiments, projection 148 moving axially down within slot 132 towards first end 101 results in projection 148 being disposed adjacent notch 115 allowing projection 148 to rotate out of slot 113 and thus allowing housing 102 to be rotatable relative sleeve 140.

Figure 8:
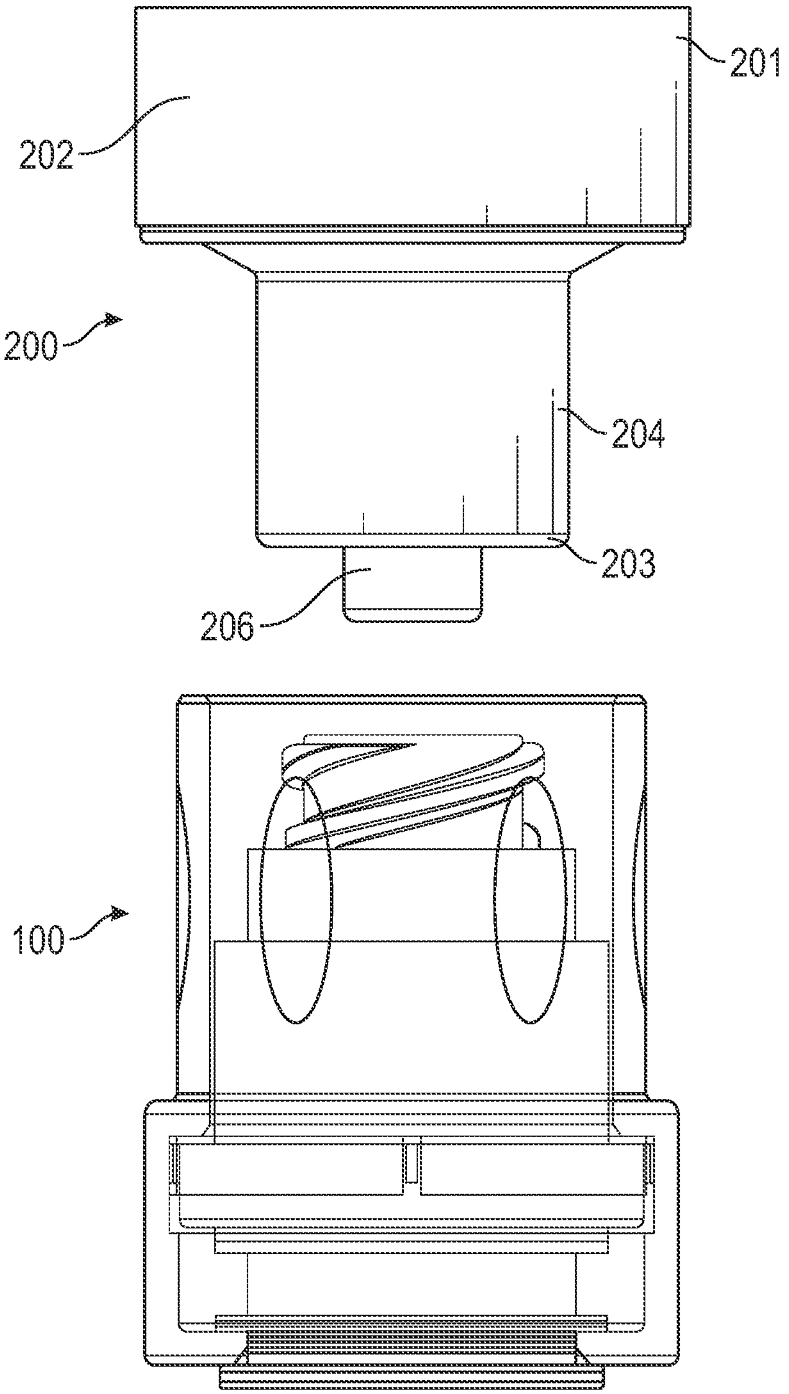
FIG. 8 is a front view of the connector of FIG. 1A and a coupling device in accordance with various aspects of the present disclosure.
Figure 9A:
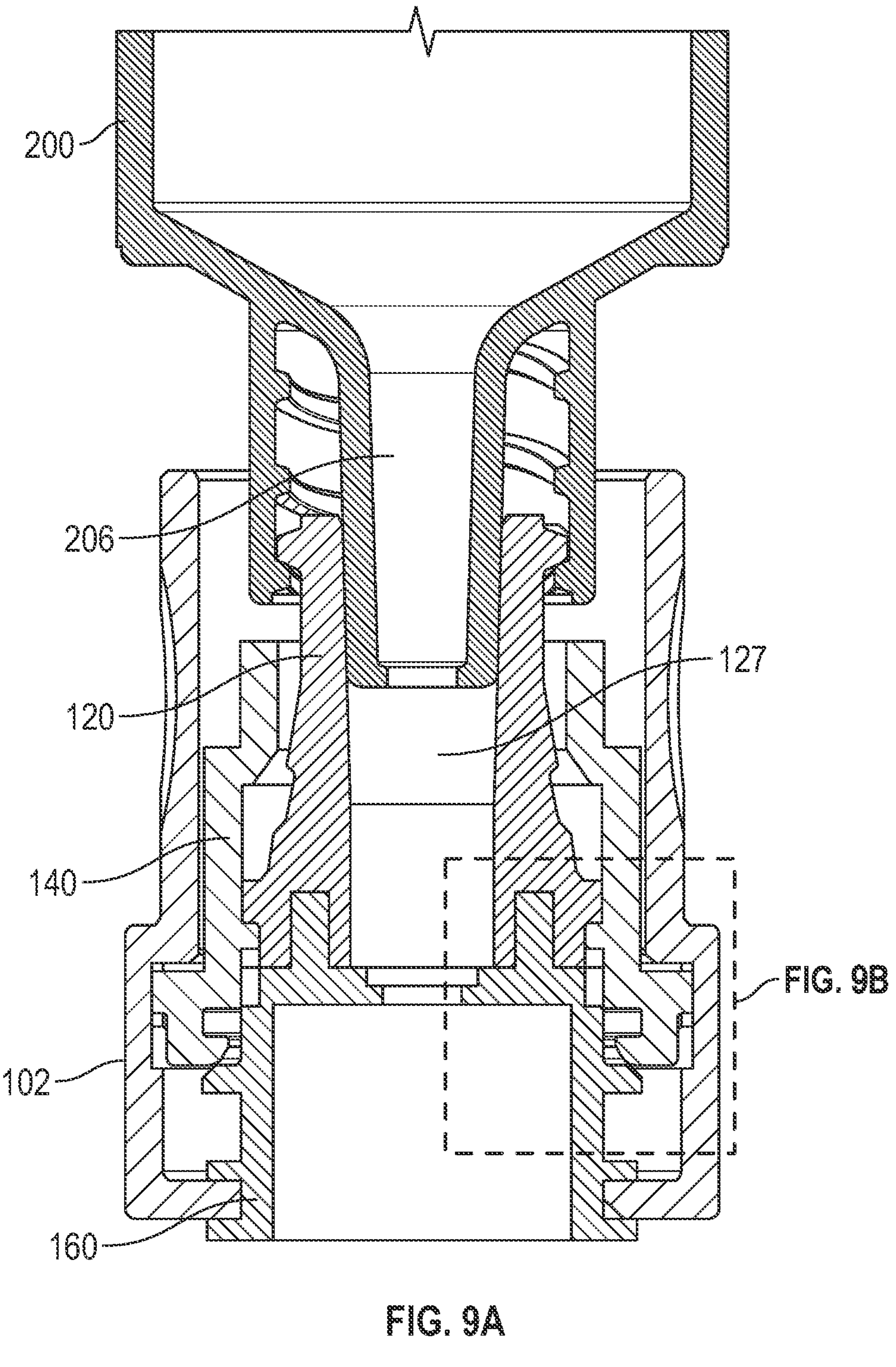
FIG. 9A is a cross-sectional view of the connector of FIG. 1 and the coupling device being partially coupled to the connector in accordance with various aspects of the present disclosure.
Figure 9B:
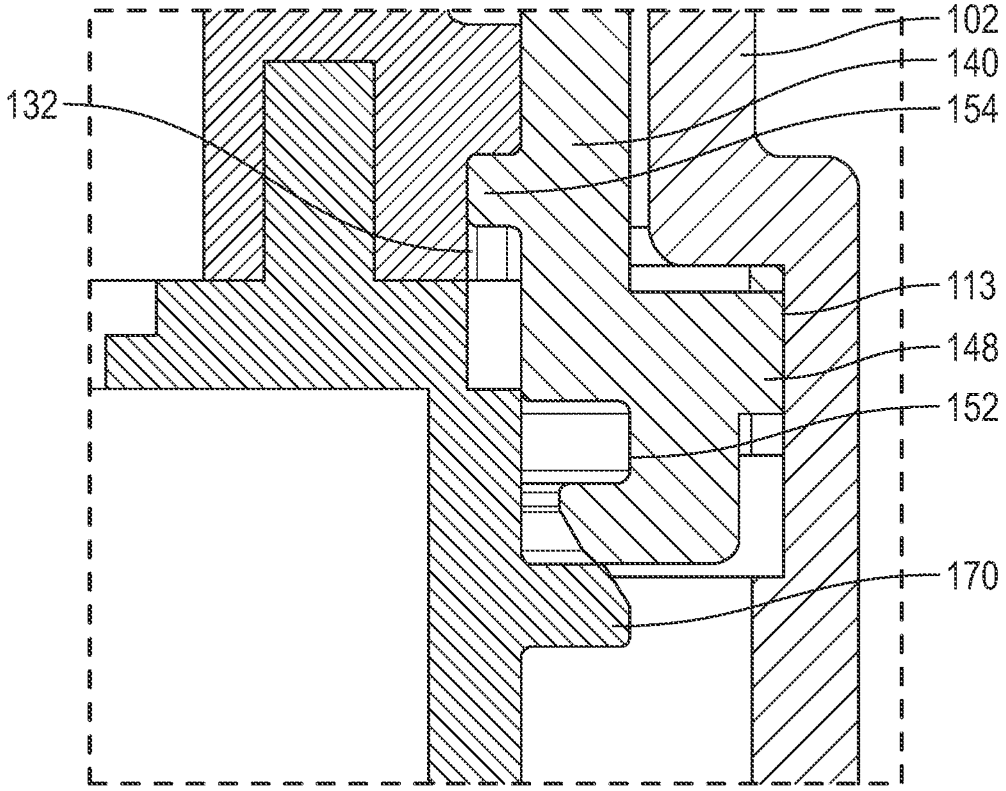
FIG. 9B is a zoomed in cross-sectional view of the connector of FIG. 9A in accordance with various aspects of the present disclosure.
Figure 10A:
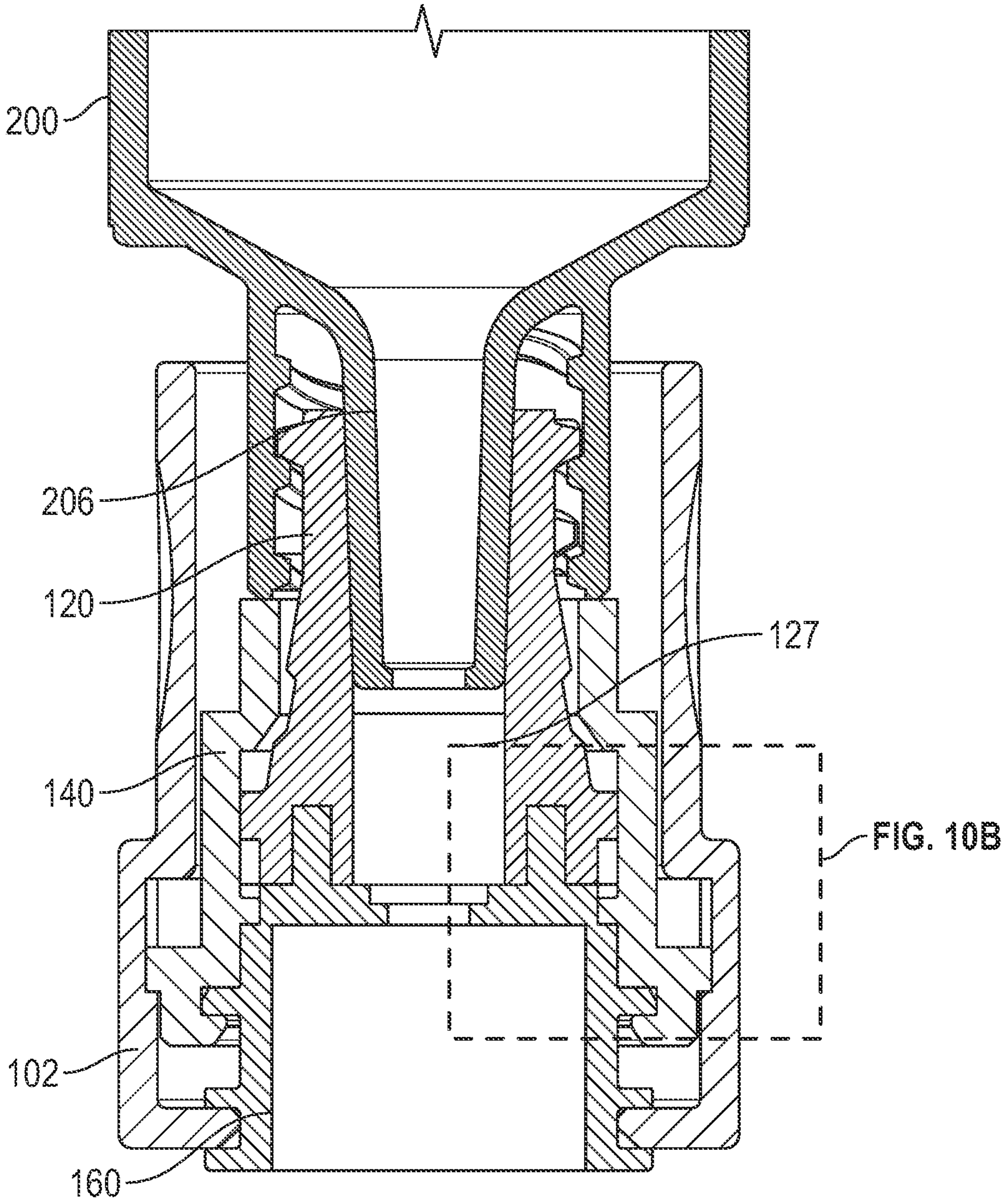
FIG. 10A is a cross-sectional view of the connector of FIG. 1A and the coupling device being fully coupled to the connector in accordance with various aspects of the present disclosure.
Figure 10B:
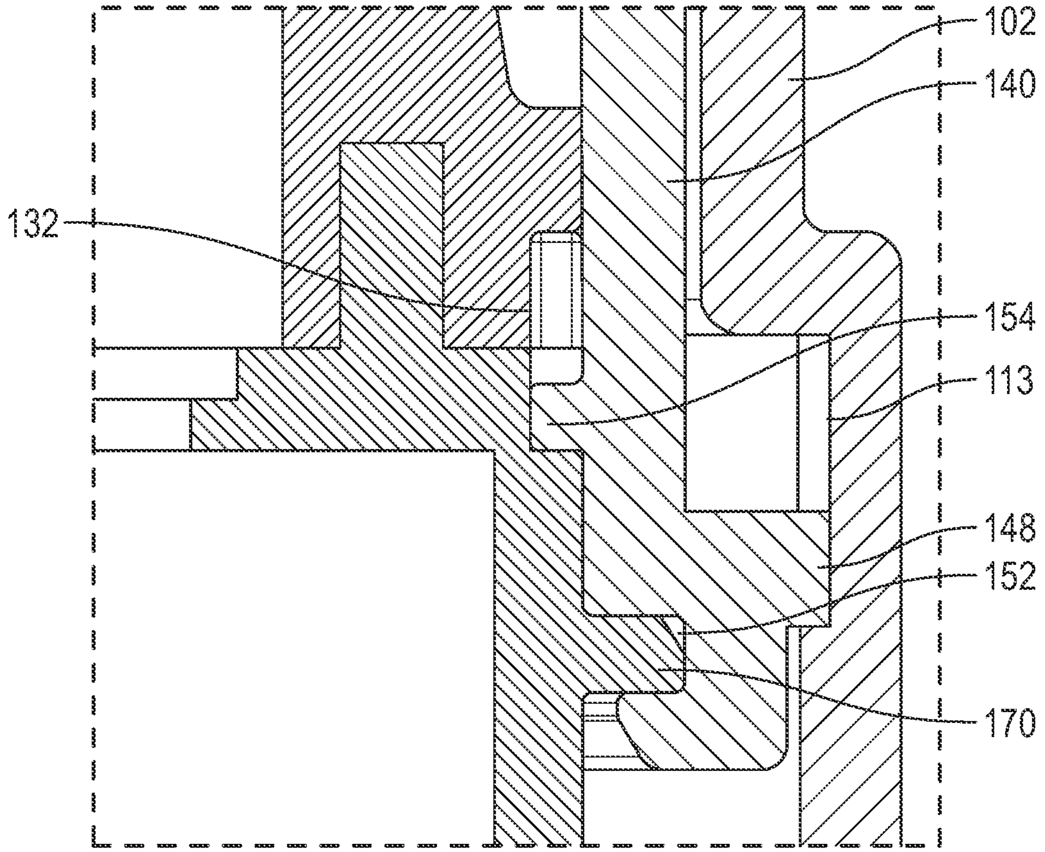
FIG. 10B is a zoomed in cross-sectional view of the connector of FIG. 10A in accordance with various aspects of the present disclosure.
Figure 11:
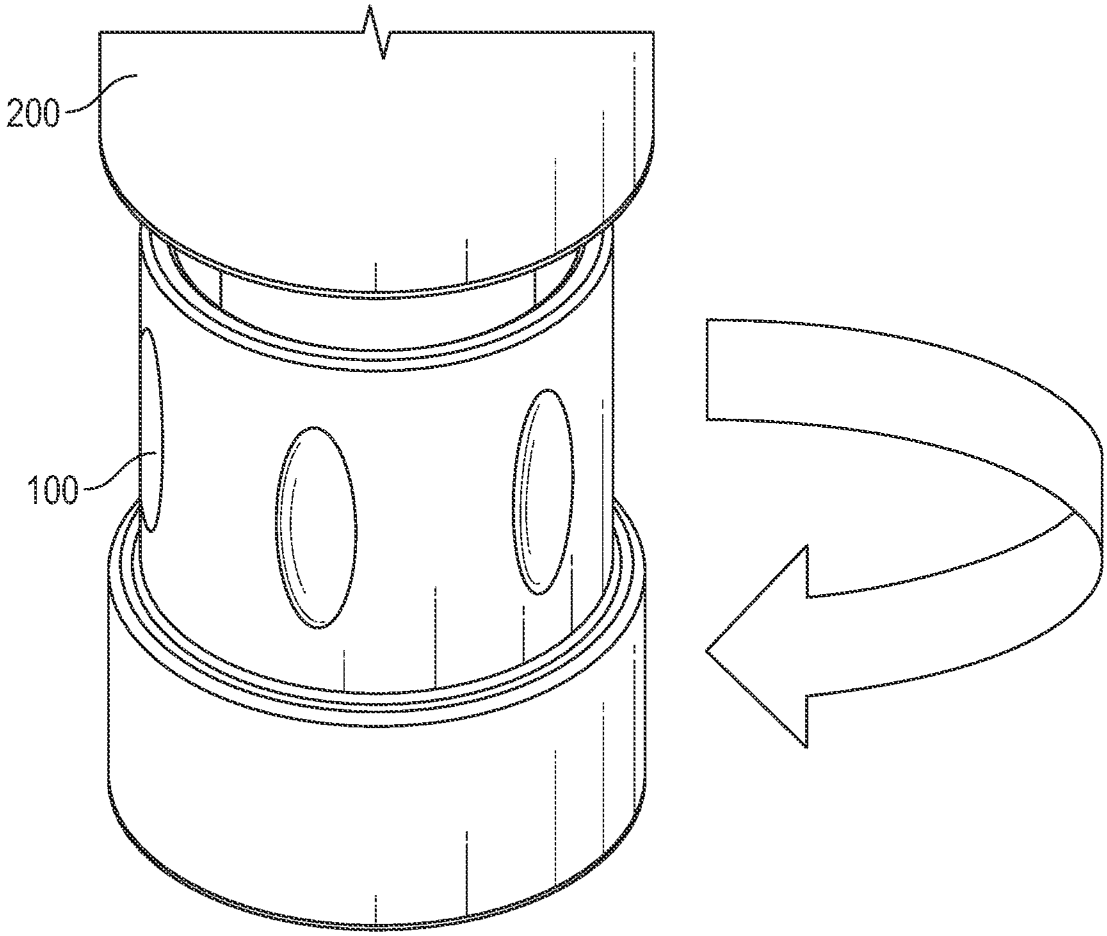
FIG. 11 is a front perspective view the connector of FIG. 1A coupled to the coupling device in accordance with various aspects of the present disclosure.

FIG. 8 is a front view of the connector of FIG. 1A and a coupling device in accordance with various aspects of the present disclosure. FIG. 9A is a cross-sectional view of the connector of FIG. 1A and the coupling device being partially coupled to the connector in accordance with various aspects of the present disclosure. FIG. 9B is a zoomed in cross-sectional view of the connector of FIG. 9A in accordance with various aspects of the present disclosure. FIG. 10A is a cross-sectional view of the connector of FIG. 1A and the coupling device being fully coupled to the connector in accordance with various aspects of the present disclosure. FIG. 10B is a zoomed in cross-sectional view of the connector of FIG. 10A in accordance with various aspects of the present disclosure. FIG. 11 is a front perspective view the connector of FIG. 1A coupled to the coupling device in accordance with various aspects of the present disclosure.

With reference to FIGS. 8-11, coupling device 200 may be configured to couple to connector 100. Coupling device 200 may be a syringe, luer, or tubing connected to a fluid source. Coupling of coupling device 200 to connector 100 results in a fluid pathway being formed between connector 100 and coupling device 200 to allow flow of fluid from a fluid source through coupling device 200 and connector 100 to a patient. In some embodiments, coupling device 200 is a male luer configured to engage with luer 120. Luer 120 may be a female luer containing threads configured to engage with coupling device 200.

Coupling device 200 may include first end 201 and second end 203 opposite first end 201. Coupling device 200 may include base 202 disposed at first end 201 and body 204 disposed proximate second end 203. In some embodiments, coupling device 200 includes tube 206. Tube 206 may extend from base 202 and may extend through body 204. In some embodiments, tube 206 is in fluid communication with base 202. Body 204 may be coupled to base 202 and circumferentially surround tube 206. Body 204 may include an inner surface having a coupling mechanism. For example, the inner surface of body 204 may include threads configured to engage with threads of coupling portion 124 of luer 120.

In some embodiments, when coupling device 200 is coupled to connector 100, tube 206 is at least partially disposed within channel 127 of luer 120. For example, coupling device 200 being coupled to luer 120 results in tube 206 at least partially being disposed within channel 127 to allow fluid to flow from a fluid source through tube 206 into channel 127 and channel 167 and out of connector 100.

Referring to FIGS. 9A-9B, coupling device 200 may rotate to threadably engage with luer 120 (e.g., coupling portion 124). For example, threads disposed on an inner surface of body 204 may engage with threads disposed on an external surface of coupling portion 124 resulting in coupling device 200 being coupled with luer 120 and tube 206 at least partially being disposed within channel 127. In some embodiments, connector 100 is configured to be in a first configuration (FIGS. 9A-9B) and second configuration (FIGS. 10A-10B). In the first configuration, coupling device 200 is decoupled or partially coupled to connector 100 via luer 120. Coupling device 200 is rotated relative to luer 120 to secure coupling device 200 to connector 100. In the first configuration, coupling device 200 is partially engaged with luer 120 and does not contact or abut sleeve 140. In the second configuration, coupling device 200 is fully engaged with luer 120 and pushes sleeve 140 down towards first end 101.

Referring to FIGS. 9A-9B, in the first configuration, locking ring 170 is not disposed within groove 152 and is disposed proximate to first end 101 compared to groove 152. Projection 154 may be disposed in slot 132 proximate luer 120 and projection 148 may be disposed within slot 113 proximate second end 101 compared to when connector 100 is in the second configuration. In the first configuration, projection 148 may not be disposed within notch 115 thereby preventing housing 102 from rotating relative to sleeve 140. In the first configuration, sleeve 140 is axial movable relative to end connector 160.

Referring to FIGS. 10A-10B, in the second configuration, locking ring 170 is disposed within groove 152. Projection 154 may be disposed in slot 132 proximate end connector 160 and projection 148 may be disposed within slot 113 proximate first end 101 compared to when connector 100 is in the first configuration. In the second configuration, projection 148 may be disposed within notch 115 thereby allowing housing 102 to rotate relative to sleeve 140. In the second configuration, sleeve 140 is prevented from axially moving relative to end connector 160.

In comparing FIG. 9B (first configuration) to FIG. 10B (second configuration), in the FIG. 9B, coupling device 200 is not contacting or pushing on sleeve 140 resulting in locking ring 170 not being disposed within groove 152. As coupling device 200 rotates and screws downward towards first end 101 relative to luer 120, coupling device 200 pushes downward on sleeve 140 causing sleeve 140 to axially move relative to luer assembly 180 and housing 102. This results in locking ring 170 being disposed within groove 152 and projection 148 moving downward ins slot 113 such that projection 148 is able to engage with notch 115.

Referring to FIG. 11, upon coupling device 200 being fully coupled and secured to connector 100 (e.g., luer 120) resulting in projection 148 being able to engage with notch 115, housing 102 is rotatable relative to sleeve 140 and luer assembly 180. Housing 102 being rotatable relative to sleeve 140 and luer assembly 180 prevents a user form rotating luer assembly 180 and sleeve 140 and thus removing coupling device 200. For example, to decouple coupling device 200 from luer 120 and thus connector 100, coupling device 200 must rotate relative to luer 120. However, in the second configuration, coupling device 200 is not rotatable relative to luer 120 as rotation of coupling device 200 causes rotation of luer 120. This allows for coupling device 200 to be non-disconnecting from luer 120 as well as being rotatable relative to housing 102.

When coupling device 200 is fully coupled to connector 100 via luer 120 (e.g., the second configuration), housing 102 becomes rotatable relative to sleeve 140 and luer assembly 180. This prevents a user from rotating coupling device 200 relative to luer 120 and thus preventing a user from decoupling coupling device 200 from connector 100. For example, due to luer 120 (and sleeve 140 and end connector 160) being disposed within housing 102 and housing 102 being rotatable relative to luer 120 (and sleeve 140 and end connector 160), a user is unable to rotate coupling device 200 relative to luer 120 since rotation of coupling device 200 causes rotation of luer 120 when connector 100 is in the second configuration. In the second configuration, a user is unable to cause coupling device 200 to rotate relative to luer 120 since rotation of coupling device 200 causes rotation of luer 120, which rotates within housing 102. A user is unable to access luer 120 since it is disposed within housing 102 and thus cannot prevent rotation of luer 120 when coupling device 200 is rotating.

In practice, if a user grasps housing 102 in attempt to rotate coupling device 200 relative to connector 100, coupling device 200, luer assembly 180, and sleeve 140 would rotate relative to housing 102 preventing a user from decoupling coupling device 200 from connector 100. Connector 100 and coupling device 200 being in the second configuration prevents decoupling of coupling device 200 from connector 100 by user. Further, connector 100 and coupling device 200 being in the second configuration prevents inadvertent decoupling of coupling device 200 from connector 100 in response to an axial force (e.g., pullout force) being applied to connector 100 and/or coupling device 200.

The disclosures described herein include at least the following clauses:

Clause 1: A connector comprising a housing having a first end and second end opposite the first end, the housing having an interior space, a luer assembly disposed within the interior space of the housing, the luer assembly having a locking ring and the luer assembly configured to couple to a coupling device to secure the coupling device to the connector, and a sleeve at least partially disposed around the luer assembly and disposed within the interior space, the sleeve configured to couple to the locking ring to prevent axial movement of the sleeve relative to the luer assembly and the housing. The housing is rotatable to the luer assembly and the sleeve when the sleeve is coupled to the locking ring to prevent decoupling of the luer assembly from the coupling device when the luer assembly is coupled to the coupling device.

Clause 2: The connector of clause 1, wherein the luer assembly includes a luer and an end connector.

Clause 3: The connector of clause 2, wherein the luer includes a coupling portion configured to couple to the coupling device.

Clause 4: The connector of clause 3, wherein the coupling portion includes a first thread configured to engage with a second thread of the coupling device.

Clause 5: The connector of clause 2, wherein the luer is coupled to the end connector such that the luer is non-rotatable relative to the end connector.

Clause 6: The connector of clause 2, wherein the housing includes a housing ring disposed at a first end and the end connector includes a base groove configured to receive and secure the housing ring to prevent axial movement of the luer assembly relative to the housing.

Clause 7: The connector of clause 2, wherein the luer includes a first channel and the end connector includes a second channel, the first channel being in fluid communication with the second channel when the luer is coupled to the end connector.

Clause 8: The connector of clause 1 further comprising a coupling device configured to couple to the luer assembly.

Clause 9: The connector of clause 8, wherein a fluid pathway is formed through the coupling device and the connector when the coupling device is coupled to the luer assembly.

Clause 10: The connector of clause 8, wherein the connector has a first configuration and a second configuration, in the first configuration the sleeve is not in contact with the coupling device and in the second configuration the sleeve is in contact with the coupling device.

Clause 11: The connector of clause 10, wherein in the second configuration, the coupling device causes the sleeve to axially move towards the second end to cause the sleeve to couple to the locking ring.

Clause 12: The connector of clause 10, wherein the coupling device and the luer assembly are rotatable relative to the housing when the connector is in the second configuration to prevent disconnecting of the coupling device from the connector.

Clause 13: The connector of clause 1, wherein the connector has a first configuration and a second configuration, in the first configuration the sleeve is not coupled to the locking ring and in the second configuration the sleeve is coupled to the locking ring.

Clause 14: The connector of clause 13, wherein the sleeve includes a projection and housing includes a slot such that the projection is disposed within the slot when the sleeve is disposed within the interior space.

Clause 15: The connector of clause 14, wherein the slot includes a notch and the projection of the sleeve is disposed within the notch when the connector is in the second configuration.

Clause 16: The connector of clause 13, wherein the sleeve and the luer assembly are rotatable relative to the housing when the connector is in the second configuration.

Clause 17: The connector of clause 1, wherein the sleeve includes a groove configured to receive the locking ring to axially fix the sleeve relative to the luer assembly.

Clause 18: The connector of clause 1, wherein the sleeve axially moves towards the second end relative to the luer assembly to couple the sleeve to the locking ring when the coupling device is coupled to the luer assembly.

Clause 19: A connector comprising a housing having a first end and second end opposite the first end, the housing having an interior space, the housing being substantially cylindrical and having a housing ring disposed at the first end, the housing ring extending radially inward into the interior space, a luer assembly disposed within the interior space of the housing, the luer assembly including a luer coupled to an end connector, the luer having coupling portion including a first thread configured to engage with a second thread of a coupling device to couple the coupling device to the luer assembly, the end connector having a base groove configured to receive the housing ring to secure the luer assembly to the housing and the end connector having a locking ring, and a sleeve at least partially disposed around the luer assembly and disposed within the interior space, the sleeve having a groove configured receive the locking ring to secure the luer assembly to the sleeve to prevent axial movement of the sleeve relative to the luer assembly and the housing. The housing is rotatable to the luer assembly and the sleeve, and the sleeve is coupled to the locking ring to prevent decoupling of the luer assembly from the coupling device when the luer assembly is coupled to the coupling device.

Clause 20: A connector comprising a housing having a first end and second end opposite the first end, the housing having an interior space, the housing being substantially cylindrical and having a housing ring disposed at the first end and extending radially inward into the interior space, the first end having a diameter greater than a diameter of the second end, a luer assembly disposed within the interior space of the housing, the luer assembly including a luer non-rotatably coupled to an end connector, the luer having coupling portion including a first thread configured to engage with a second thread of a coupling device to couple the coupling device to the luer assembly, the end connector having a base groove configured to receive the housing ring to secure the luer assembly to the housing and the end connector having a locking ring, wherein the luer includes a first channel and the end connector includes a second channel, the first channel being in fluid communication with the second channel when the luer is coupled to the end connector, and a sleeve at least partially disposed around the luer assembly and disposed within the interior space, the sleeve having a groove configured receive the locking ring to secure the luer assembly to the sleeve to prevent axial movement of the sleeve relative to the luer assembly and the housing, the sleeve having a projection configured to engage with a slot of the housing when the sleeve is disposed within the interior space. The connector has a first configuration and a second configuration, in the first configuration the sleeve is not coupled to the locking ring and in the second configuration the sleeve is coupled to the locking ring. The sleeve axially moves towards the second end relative to the luer assembly to couple the sleeve to the locking ring when the coupling device is coupled to the luer assembly. The housing is rotatable to the luer assembly and the sleeve, and the sleeve is coupled to the locking ring to prevent decoupling of the luer assembly from the coupling device when the connector is the second configuration. A fluid pathway is formed through the coupling device and the connector when the connector is the second configuration.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A connector comprising:

a housing having a first end, second end opposite the first end, and an interior space;

a luer assembly disposed within the interior space of the housing, the luer assembly having a locking ring and the luer assembly configured to couple to a coupling device to secure the coupling device to the connector; and a sleeve at least partially disposed around the luer assembly and disposed within the interior space, the sleeve configured to axially move towards the second end and couple to the locking ring when the coupling device is coupled to the luer assembly, to prevent axial movement of the sleeve relative to the luer assembly and the housing, wherein the housing is rotatable relative to the luer assembly and the sleeve when the sleeve is coupled to the locking ring to prevent decoupling of the luer assembly from the coupling device when the luer assembly is coupled to the coupling device.

2. The connector of claim 1, wherein the luer assembly includes a luer and an end connector.

3. The connector of claim 2, wherein the luer includes a coupling portion configured to couple to the coupling device.

4. The connector of claim 3, wherein the coupling portion includes a first thread configured to engage with a second thread of the coupling device.

5. The connector of claim 2, wherein the luer is coupled to the end connector such that the luer is non-rotatable relative to the end connector.

6. The connector of claim 2, wherein the housing includes a housing ring disposed at the first end and the end connector includes a base groove configured to receive and secure the housing ring to prevent axial movement of the luer assembly relative to the housing.

7. The connector of claim 2, wherein the luer includes a first channel and the end connector includes a second channel, the first channel being in fluid communication with the second channel when the luer is coupled to the end connector.

8. The connector of claim 1 further comprising:

the coupling device configured to couple to the luer assembly.

9. The connector of claim 8, wherein a fluid pathway is formed through the coupling device and the connector when the coupling device is coupled to the luer assembly.

10. The connector of claim 8, wherein the connector has a first configuration and a second configuration, in the first configuration the sleeve is not in contact with the coupling device and in the second configuration the sleeve is in contact with the coupling device.

11. The connector of claim 10, wherein in the second configuration, the coupling device causes the sleeve to axially move towards the second end to cause the sleeve to couple to the locking ring.

12. The connector of claim 10, wherein the coupling device and the luer assembly are rotatable relative to the housing when the connector is in the second configuration to prevent disconnecting of the coupling device from the connector.

13. The connector of claim 1, wherein the connector has a first configuration and a second configuration, in the first configuration the sleeve is not coupled to the locking ring and in the second configuration the sleeve is coupled to the locking ring.

14. The connector of claim 13, wherein the sleeve includes a projection and housing includes a slot such that the projection is disposed within the slot when the sleeve is disposed within the interior space.

15. The connector of claim 14, wherein the slot includes a notch and the projection of the sleeve is disposed within the notch when the connector is in the second configuration.

16. The connector of claim 13, wherein the sleeve and the luer assembly are rotatable relative to the housing when the connector is in the second configuration.

17. The connector of claim 1, wherein the sleeve includes a groove configured to receive the locking ring to axially fix the sleeve relative to the luer assembly.

18. A connector comprising:

a housing having a first end and second end opposite the first end, the housing having an interior space, the housing being cylindrical and having a housing ring disposed at the first end, the housing ring extending radially inward into the interior space;

a luer assembly disposed within the interior space of the housing, the luer assembly including a luer coupled to an end connector, the luer having coupling portion including a first thread configured to engage with a second thread of a coupling device to couple the coupling device to the luer assembly, the end connector having a base groove configured to receive the housing ring to secure the luer assembly to the housing and the end connector having a locking ring; and a sleeve at least partially disposed around the luer assembly and disposed within the interior space, the sleeve having a groove configured receive the locking ring to secure the luer assembly to the sleeve to prevent axial movement of the sleeve relative to the luer assembly and the housing, wherein the housing is rotatable to the luer assembly and the sleeve, and the sleeve is coupled to the locking ring to prevent decoupling of the luer assembly from the coupling device when the luer assembly is coupled to the coupling device.

19. A connector comprising:

a housing having a first end and second end opposite the first end, the housing having an interior space, the housing being cylindrical and having a housing ring disposed at the first end and extending radially inward into the interior space, the first end having a diameter greater than a diameter of the second end;

a luer assembly disposed within the interior space of the housing, the luer assembly including a luer non-rotatably coupled to an end connector, the luer having coupling portion including a first thread configured to engage with a second thread of a coupling device to couple the coupling device to the luer assembly, the end connector having a base groove configured to receive the housing ring to secure the luer assembly to the housing and the end connector having a locking ring, wherein the luer includes a first channel and the end connector includes a second channel, the first channel being in fluid communication with the second channel when the luer is coupled to the end connector; and a sleeve at least partially disposed around the luer assembly and disposed within the interior space, the sleeve having a groove configured receive the locking ring to secure the luer assembly to the sleeve to prevent axial movement of the sleeve relative to the luer assembly and the housing, the sleeve having a projection configured to engage with a slot of the housing when the sleeve is disposed within the interior space, wherein the connector has a first configuration and a second configuration, in the first configuration the sleeve is not coupled to the locking ring and in the second configuration the sleeve is coupled to the locking ring, wherein the sleeve axially moves towards the second end relative to the luer assembly to couple the sleeve to the locking ring when the coupling device is coupled to the luer assembly, wherein the housing is rotatable to the luer assembly and the sleeve, and the sleeve is coupled to the locking ring to prevent decoupling of the luer assembly from the coupling device when the connector is the second configuration, wherein a fluid pathway is formed through the coupling device and the connector when the connector is the second configuration.

* * * * *